United States Patent [19]

Cabal et al.

[11] 4,291,691
[45] Sep. 29, 1981

[54] COMBINED RESPIRATOR AND CATHETER SUCTION ADAPTER

[75] Inventors: Luis A. Cabal, Pasadena, Calif.; Carmelo P. Dali, Chesire, Conn.

[73] Assignee: Novametrix Medical Systems, Inc., Wallingford, Conn.

[21] Appl. No.: 955,514

[22] Filed: Oct. 30, 1978

[51] Int. Cl.³ ............................................. A61M 25/00
[52] U.S. Cl. ......................... 128/204.18; 128/207.14; 128/912; 128/276; 128/247; 128/350 R; 128/205.24; 285/121; 285/122; 285/133 R; 285/DIG. 2
[58] Field of Search ........ 128/349 BV, 349 B, 349 R, 128/348, 350 R, 350 V, 347, DIG. 9, 274, 276, 203.25, 204.25, 205.11, 207.14, 207.15, 207.16; 251/145; 285/DIG. 2, 121, 122, 123, 124, 127, 133 R

[56] References Cited

U.S. PATENT DOCUMENTS

| | | | |
|---|---|---|---|
| 2,357,755 | 9/1944 | Moll | 285/127 |
| 2,912,982 | 11/1959 | Barsky | 128/351 |
| 3,322,126 | 5/1967 | Rüsch et al. | 128/351 |
| 3,699,964 | 10/1972 | Ericson | 128/274 X |
| 3,707,972 | 1/1973 | Villari et al. | 128/349 R |
| 3,800,799 | 4/1974 | McWhorter | 128/247 X |
| 3,834,388 | 9/1974 | Sauer | 128/276 |
| 4,026,284 | 5/1977 | Boehringer | 128/276 X |

FOREIGN PATENT DOCUMENTS

216569 3/1958 Australia ............................ 128/351

Primary Examiner—Henry J. Recla
Attorney, Agent, or Firm—Howard F. Mandelbaum

[57] ABSTRACT

An adapter to be connected between a respirator and a patient artificial airway has an axial bore communicating between the respirator and artificial airway and one or more sloping bores communicating between the axial bore and the periphery of the adapter body to provide one or more respective access openings leading to the bore through which a suction catheter can be inserted. Means for sealing the access openings from the ambient environment when a suction catheter is not in use is provided by an access closure means which includes a member movable on the adapter body and an elastomeric sealing means which is compressed about each access opening to form an airtight seal when the access closure means is in a position to cover the access openings. Each access opening can accept a catheter for insertion through the axial bore and into the artificial airway when the access closure means is in a position to expose the access opening. The access closure means may include a member that is slidable or rotatable or slidable and rotatable, or pivotal with respect to the valve body. A resilient tab can be disposed between the movable member of the access closure means and the elastomeric sealing means which is normally urged away from the sealing means when out of contact with the movable member and which is urged against the sealing means when the movable member is moved into a covering position to close the valve.

18 Claims, 13 Drawing Figures

COMBINED RESPIRATOR AND CATHETER SUCTION ADAPTER

BACKGROUND OF THE INVENTION

Some patients having respiratory problems are assisted in breathing by a mechanical respirator which pumps ambient or oxygen enriched air directly into the lungs of the patient through an artificial airway which can include an endotracheal tube, nasal prongs or a tracheotomy tube. The artificial airway is connected to the respirator by means of an adapter. The adapter is affixed to the artificial airway at one end and removably connected to the respirator at the other end. As a result of a lack of coughing and of adequate airway humidification as well as a side effect of administration of gases, accumulation of secretions in the lungs may occur. The removal of these secretions is necessary for adequate oxygenation and ventilation as well as to prevent asphyxiation due to physical partial blockage or complete obstruction of the artificial airway. The removal of such secretions requires that a catheter connected to a source of vacuum be inserted into the lungs to remove the fluids by suction. Such suctioning, which is commonly performed at various intervals, is accomplished by inserting the suction catheter through the artificial airway into the lungs. In order to insert the catheter into the artificial airway it is necessary to disconnect it from the respirator to provide an access opening for the catheter. The connector by which the artificial airway is attached to the respirator cooperates with a fitting on the respirator which permits the connector to be readily coupled to and removed from the respirator. However, when the connector is removed from the respirator to permit insertion of the catheter for fluid suctioning, the patient may be deprived of oxygen until suctioning is completed, the catheter is withdrawn from the artificial airway and the connector is again attached to the respirator. In addition, the patient may be apneic or develop apnea upon disconnection of the airway from the respirator that precludes any air exchange during the airway suction. Suctioning typically takes a period of time on the order of one minute during which the patient is unable to breath.

It may also be desirable to sample the air flowing to the patient from the respirator through the artificial airway to monitor the temperature of the air, various pressures, flow rates and volumes, as well as the exhaled carbon dioxide and other gases. Gas flow, volume pressure and temperature measurements require the insertion of auxiliary fittings and/or adaptors between the artificial airway and the respirator connector adaptor or between the connector adaptor and the respirator itself.

Attempts have been made to provide a respirator connector and valve to permit fluid suctioning without interruption of the patient's breathing but the apparatuses resulting from such attempts to date have been complex, costly to fabricate, difficult to use, and of questionable reliability and safety. Some have required separate channels for oxygen flow and fluid suctioning. Others have required troublesome mechanical assemblies to assist movement of the catheter through the artificial airway.

SUMMARY OF THE INVENTION

The foregoing problems are overcome by the invention which includes an adapter assembly adapted to be connected between a respirator and an artificial airway inserted into the trachea of a patient and having an axial bore for the passage of air and oxygen and exhaled gases between the patient and respirator and one or more inclined bores communicating between an access opening on the periphery of the adapter body and the axial bore. The angle of the inclined bores with respect to the axial bore is selected to permit insertion of a catheter through one of the inclined bores into the axial bore and through the artificial airway with no binding or snagging and a minimum of friction so that the physician applying the catheter can feel when the desired point of full insertion of the catheter has been reached. Means for covering the access opening when the catheter is not being used in order to form an airtight seal over the access opening so that there is no leakage of the gases flowing between the respirator and patient include an elastomeric seal on the surface of the adapter body adjacent to the access opening and a movable member adapted to cooperate with the seal to selectively expose the access opening when suctioning is not being done.

Four embodiments of the invention are disclosed. In the first embodiment a cylindrical collar coaxial with and rotatable about the cylindrical body of the adapter has an aperture which can be brought into or out of registration with the access opening in the adapter body by rotation. The seal comprises an elastomeric sleeve disposed between the collar and adapter body and having an aperture in registration with the access opening in the body. In the second embodiment the seal is formed by two elastomeric rings axially spaced on either side of the access openings on the body and the collar is axially slidable for alternately exposing and covering the access openings and rotatable for locking the collar to prevent unwanted axial motion. The third embodiment employs a resilient arcuate tab normally urged away from an elastomeric seal framing the access openings in the body and a slidable member which when slid over the tab urges it against the elastomeric seal to compress it about the access openings for preventing gas leakage. The fourth embodiment employs independently pivotal arms which can be swung between positions covering and exposing a respective access opening.

It is therefore an object of the invention to provide a respirator-suction adapter through which a catheter can be applied for suctioning fluid accumulations in the lungs of a patient without interrupting the patient's breathing.

Another object of the invention is to provide a respirator-suction adapter through which the catheter can be inserted without snagging or binding and with a minimum of friction.

Still another object of the invention is to provide a respirator-suction adapter which can be simply constructed at low enough cost to permit discarding of the adapter after relatively short use.

A further object of the invention is to provide a respiration-suction adapter having an access opening for permitting insertion of a catheter for suctioning fluids from the lungs of a patient and means for forming an airtight seal over said access opening to prevent gas leakage through it between suctioning intervals.

Still a further object of the invention is to provide a respirator-suction adapter which can provide a sampling point for other measurements.

Other and further objects of the invention will be apparent from the following drawings and description of four preferred embodiments of the invention in which like parts are indicate by like reference numbers in the various views.

DESCRIPTION OF THE PREFERRED EMBODIMENTS

Referring now to FIGS. 1-4 of the drawings there is shown a cylindrical adapter body 1 having an upper portion 3 of enlarged diameter, a middle portion 5 of smaller diameter than the upper portion 3 and a tapered narrow portion 7 to which there is connected a tapered fitting 9 having a flange 11. The tapered fitting 9 is adapted to engage the respirator end of an artificial airway inserted into the trachea of a patient whose breathing is to be assisted by the respirator. The artificial airway can include an endotracheal tube, nasal prongs or a tracheotomy tube.

Figure 1:
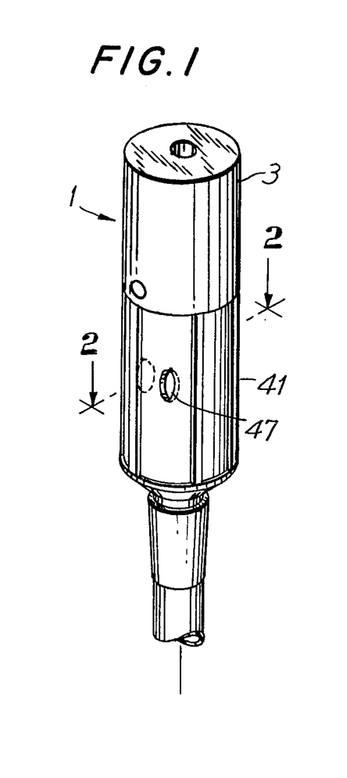
FIG. 1 is a perspective view of a first embodiment of the invention in one state of operation.
Figures 2, 3, 4:
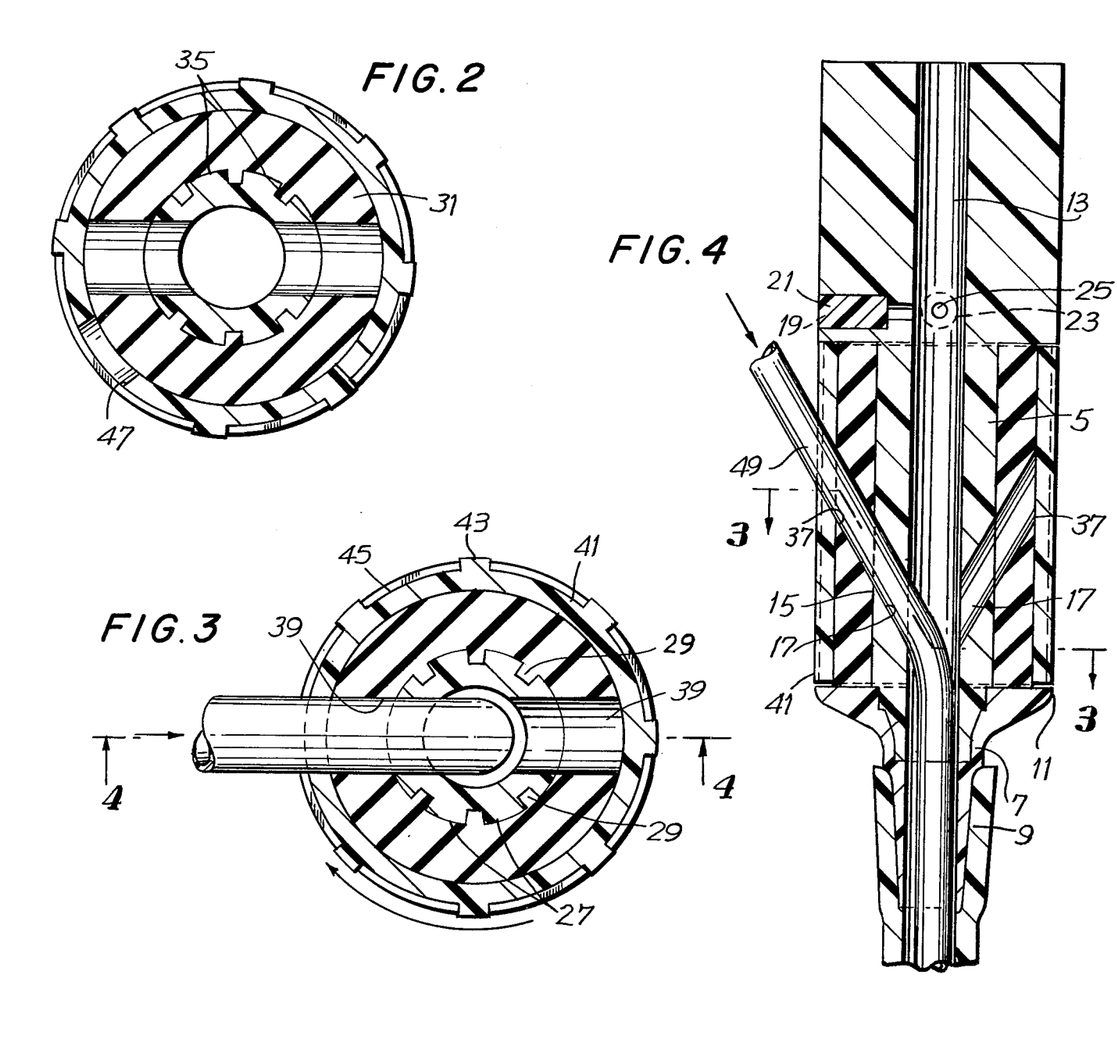
FIG. 2 is a sectional plan view of the first embodiment of the invention taken through line 2—2 of FIG. 1.
FIG. 3 is a sectioned plan view of the first embodiment of the invention in another state of operation taken through line 3—3 of FIG. 4.
FIG. 4 is a sectioned elevation view of the first embodiment of the invention taken through line 4—4 of FIG. 3.
Figures 5, 6, 7:
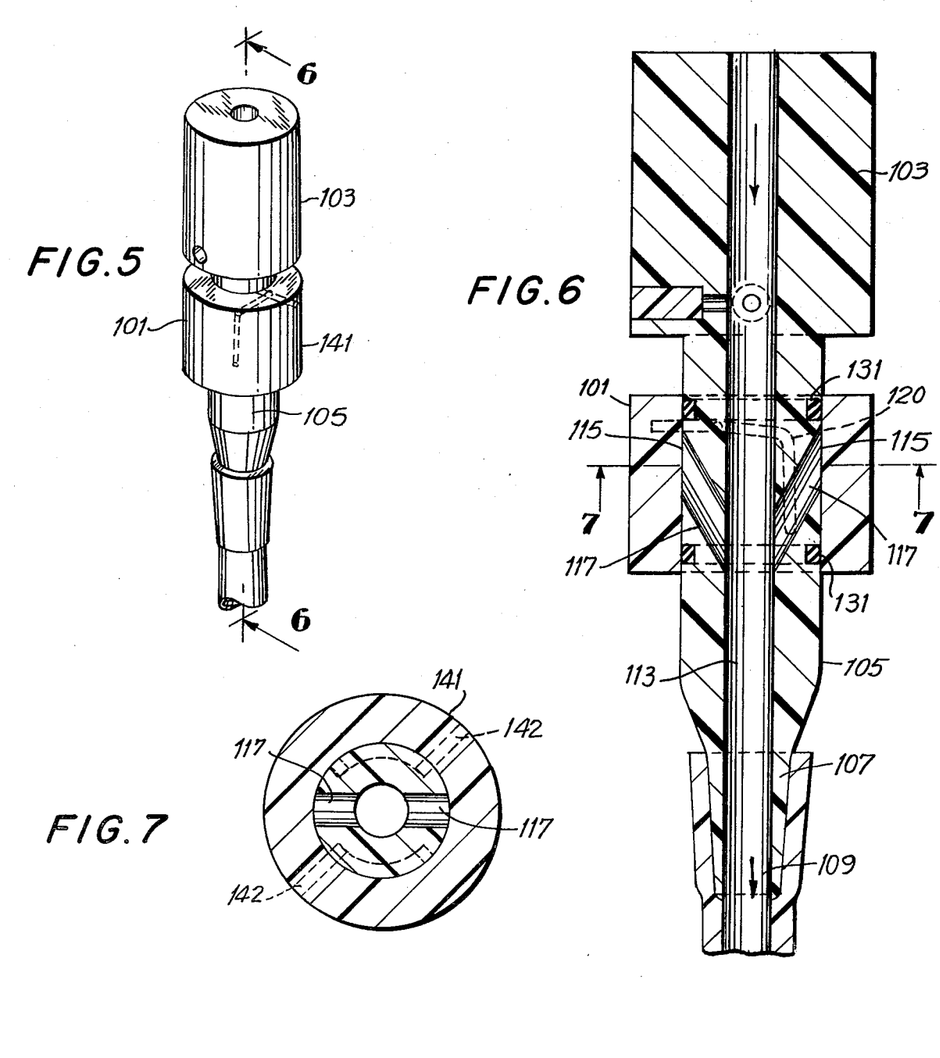
FIG. 5 is a perspective view of a second embodiment of the invention in one state of operation.
FIG. 6 is a sectioned elevation view of the second embodiment of the invention taken through line 6—6 in FIG. 5.
FIG. 7 is a sectioned plan view of the second embodiment of the invention taken through line 7—7 of FIG. 6.
Figure 8:
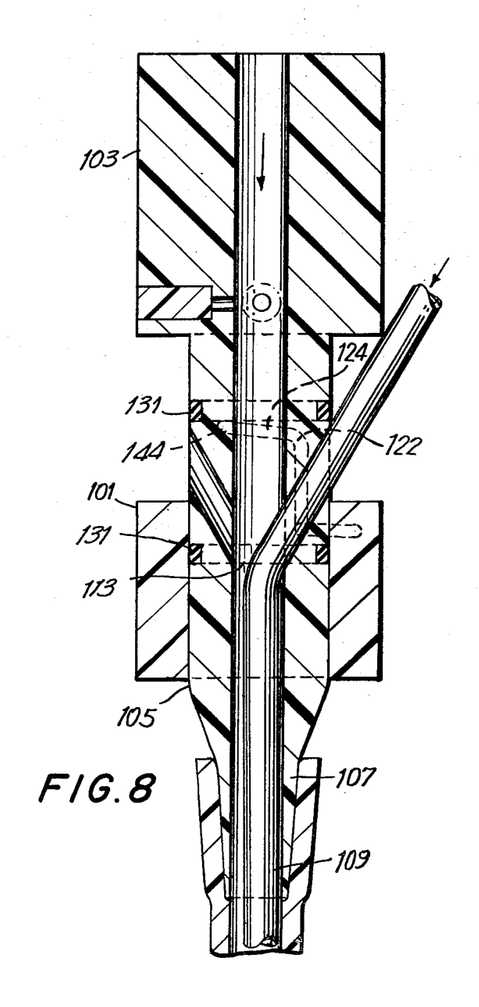
FIG. 8 is a sectioned elevation view of the second embodiment of the invention in another state of operation.

The adapter body 1 has an axial bore 13 running its full length for permitting flow of gases between the respirator and the artificial airway. Extending through the middle portion 5 of the adapter body 1 between access openings 15 and the axial bore 13 are inclined or sloping diametrically opposite bores 17. The bores 17 are of sufficient diameter to permit a catheter used to suction fluid from the lungs and bronchial passages of a patient to be inserted at the access openings 15 through the inclined bores 17 and through the axial bore 13 into the artificial airway. The angle between the axis of the central bore 13 and the axes of the sloping bores 17 as shown in FIG. 4 is approximately 20 degrees. This angle has been found to be desirable in permitting the catheter to be inserted through one of the access openings 15 and downward through the axial bore 13 without binding or snagging and permits the physician applying the catheter to feel when the suctioning end of the catheter has engaged the bodily tissue of the patient so that insertion of the catheter can be halted before possible injury to the patient which could occur if the catheter were overextended into the body.

Too small an angle between the respective axes of the inclined bores 17 and the central bore 13 requires that the length of the adapter body be enlarged. Enlargement of the length of the adapter has several disadvantages. First, the amount of dead air space and the exhaled air which the patient rebreathes increases with the length of the valve. It is desirable to minimize the amount of dead air space so that only air processed by the respirator is injected into the patient's lungs and exhaled air is excluded. Also, when applied to newborn children (neonates) an elongated adapter body becomes difficult to manage due to its bulk relative to the size of the neonate and the neonatal environment.

Too large an angle between the axis of the central bore 13 and the axes of the inclined bores 17 causes the catheter when inserted through the access openings 15 to engage the opposite wall of the inner bore 13 at too steep an angle thereby resulting in binding or snagging of the suction end of the catheter against the adapter wall. In practice it has been found desirable to maintain the angle between the axis of the central bore 13 and the axes of the inclined bores 17 between 20 degrees and 35 degrees. Although the illustrated embodiment of the invention show two diametrically opposite inclined bores 17 for inserting a catheter only one inclined bore need be used, the two being somewhat preferable in reducing the amount of rotation of the adapter body necessary when applying the catheter when an access opening 15 is not conveniently facing in a direction at which it is desired to apply the catheter.

It is sometimes desirable to be able to provide communication between the gas or air flow through the central bore 13 and an external measuring device for monitoring such parameters as temperature and pressure of the air and gases passing through the adapter body 1 between the respirator and patient. To facilitate the application of an external measuring instrument, the enlarged portion 3 of the adapter body 1 is provided with a radial bore 19 extending from an auxiliary opening 21 on the periphery of the enlarged portion 3 of the adapter body 1 to the axial bore 13. A second radial bore 23 extending between a second auxiliary opening 25 and the axial bore 13 can also be provided on the enlarged portion 3 of the adapter body 1 to permit simultaneous measurement of two parameters, as for example, temperature and pressure. The radial bores 19 and 23 may interface at the periphery of the enlarged portion 3 of the adapter body 1 with tubes or sensors which are connected to external measuring apparatus. To prevent gas leakage from the central bore 13 through the radial bores 21 and 23, each of the auxiliary openings 21 and 25 can be fitted with a removable plug or can be provided with an elastomeric diaphragm held in place by a retaining ring or by other means known to the art.

The periphery of the middle section 5 of the adapter body 1 is provided with alternating ribs 27 and grooves 29 running lengthwise parallel to the axis of the adapter body 1. Disposed about the middle portion 5 of the adapter body 1 is a hollow cylindrical sleeve 31 made from an elastomeric material such as rubber. Running longitudinally along the interior wall of the elastomeric sleeve 31 are alternating ribs 33 and grooves 35. The sleeve 31 has two diametrically opposed access openings 37 which communicate with the central bore of the sleeve 31 through inclined bores 39. The angle of inclination of the axes of the inclined bores 39 with respect to the axis of the central bore of the sleeve 31 is preferably the same as the angle of inclination between the inclined and axial bores of the adapter body 1.

The elastomeric sleeve 31 is disposed about the circumference of the middle portion 5 of the adapter body 1 with the ribs 33 and grooves 35 of the sleeve 31 respectively engaging the grooves 29 and ribs 27 of the middle section 5 of the adapter body 1 to prevent relative rotation between the adapter body 1 and the elastomeric sleeve 31. The sleeve 31 may be slid over the tapered portion 7 of the adapter body 1 and onto the middle portion 5 prior to attaching the tapered fitting 9.

The length of the elastomeric sleeve 31 is preferably equal to the distance between the shoulder which separates the enlarged portion 3 from the middle portion 5 of the adapter body 1 and the flange 11 of the tapered fitting 9. The inclined bores 39 of the sleeve 31 are axially positioned so that they are coaxial with the axes of respective inclined bores 17 of the middle section 5 of the adapter body 1 when the sleeve 31 is in circumscribing position on the middle section 5 of the adapter body 1 as shown in FIGS. 1-4.

A hollow cylindrical collar 41 has an inner diameter slightly smaller than the uncompressed outer diameter of the cylindrical sleeve 31. The cylindrical collar 41 is rotatably supported on the periphery of the elastomeric sleeve 31 between the shoulder separating enlarged portion 3 and middle portion 5 of the adapter body 1 and flange 11 of tapered fitting 9. The outer diameter of the sleeve 31 and inner diameter of the collar 41 are chosen to provide enough friction between the cylindrical surface of the elastomeric sleeve 31 and the bore of the collar 41 to prevent inadvertent rotation or slippage of the collar 41 with respect to the sleeve 31 but not so much friction as would interfere with intentional rotation of the collar 41 with respect to the sleeve 31 by the fingers of the user. The collar 41 is provided with alternating longitudinal ribs 43 and grooves 45 on its periphery to provide a gripping surface for the fingers of the user during rotation of the collar.

An access opening 47 is provided in the outer wall of the cylindrical collar 41 and communicates with the central bore of the collar 41 through an inclined bore 49 in the wall of the collar 41. The angle of the axis of the inclined bore 49 with respect to the axis of the central bore of the cylindrical collar 41 is preferably substantially the same as the angles between the axes of the inclined bores and central bores of the sleeve 31 and adapter body 1. The inclined bore 49 is located longitudinally in the wall of the collar 41 so that it shares a common axis with the inclined bores of the sleeve 31 and middle portion 5 of the adapter body 1 as shown in FIG. 4. The length of the collar 41 is substantially the same as or slightly less than the length of the elastomeric sleeve 31. In assembly, the collar 41 can be slipped over the periphery of the elastomeric sleeve 31 and the tapered fitting 9 can then be attached with the flange 11 of the tapered fitting 9 abutting the opposing circular face of the cylindrical elastomeric sleeve 31. The elastomeric sleeve 31 is normally compressed between the periphery of the middle portion 5 of the adapter body 1 and the interior cylindrical surface of the collar 41 with the access opening 47 in the collar 41 out of registration with the access openings 37 and 15 in the sleeve 31 and the middle portion 5 of the adapter body 1 respectively as shown in FIG. 2. In this state, air and body gases can flow between the respirator and patient with substantially no leakage from the adapter body 1. When it is desired to suction the patient to remove accumulated fluids the collar 41 can be grasped between the thumb and forefinger of the user and rotated relative to the elastomeric sleeve 31 and adapter body 1 to bring the access opening 47 of collar 41 into registration with the access opening 37 of the sleeve 31 as shown in FIG. 2. The catheter can then be inserted through the coaxial inclined bores 49, 39 and 17, into and through the central bore 13 of the adapter body and out through the tapered fitting 9 and through the artificial airway into the trachea of the patient. The unexpanded access opening 37 in the sleeve 31 can be just slightly smaller than the outer diameter of the catheter used so that a substantially airtight seal is formed between the elastomeric sleeve 31 and the engaged outer wall of the catheter to minimize air and gas leakage during suctioning thereby avoiding interference with the patient's breathing. The access opening 37 in the sleeve 31 should not be so small as to provide friction between the sleeve 31 and catheter which could interfere with the "feel" of the catheter as it is inserted into its rest position within the body of the patient.

The adapter body 1, collar 41 and tapered fitting 9 are preferably made of a rigid plastic suitable for injection molding and sterilizable. The rubber from which sleeve or seal 31 is formed should be flexible and resilient relative to the material used in the adapter body 1 and collar 41 but should not be so soft that it will snag or tear when engaged by the catheter or the rotating collar 41.

A second embodiment of the invention will now be described with reference to FIGS. 5-8 in which there is shown an adapter body 101 having an enlarged portion 103 adapted to be removably connected to a respirator, a middle body portion 105 and a tapered portion 107 terminating in a tapered fitting 109. The adapter body 101 has an axial bore 113 and access openings 115 communicating with the axial bore 113 through inclined or sloping bores 117 similar to those described in connection with the first embodiment of the invention.

Also formed within the middle portion 105 of the adapter body 101 are diametrically opposed grooves 120 partially penetrating the circumferential wall of the adapter body middle portion 105, each of the grooves 120 having an axially extending section 122 terminating at the respirator end of the adapter in a circumferentially extending section 124.

Circumferential grooves are provided on the outer cylindrical wall of the adapter body middle section 105 in parallel planes transverse to the axis of the body 101 and spaced from the groove 120 to receive respective elastomeric O-rings 131. The outer circumference of the O-rings 131 when disposed in their respective grooves on the surface of the adapter body middle section 105 are slightly greater than the outer circumference of the adapter body middle section 105.

The circumference of the adapter body middle portion 105 may taper inwardly slightly from the respirator end to the artificial airway end for reasons which will be explained.

A hollow cylindrical collar 141 has an inner diameter slightly greater than the outer diameter of the adapter body middle portion section 105 and when used with an adapter body 101 having a tapered middle portion 105 can have a slightly conical bore conforming to the taper of the adapter body middle portion so that as the collar 141 is moved axially from the artificial airway end of the adapter body 101 toward the respirator end it engages the surface of the adapter body middle portion 105 and, in particular, the outer surfaces of the O-rings 131 with increasing friction thereby compressing the O-rings 131 so that an airtight seal is formed between the adapter body middle portion 105, O-rings 131, and cylindrical collar 141.

The cylindrical collar 141 has, extending radially inwardly from diametrically opposite points on its interior cylindrical wall pins 142 which are disposed and ride in the respective grooves 120. The pins and grooves cooperate to limit the distance of relative axial movement between the collar 141 and adapter body 101 to the length of the axial groove sections 122 and to limit rotational movement to the arc length of the circumferential groove sections 124.

Figures 9, 10, 11, 12:
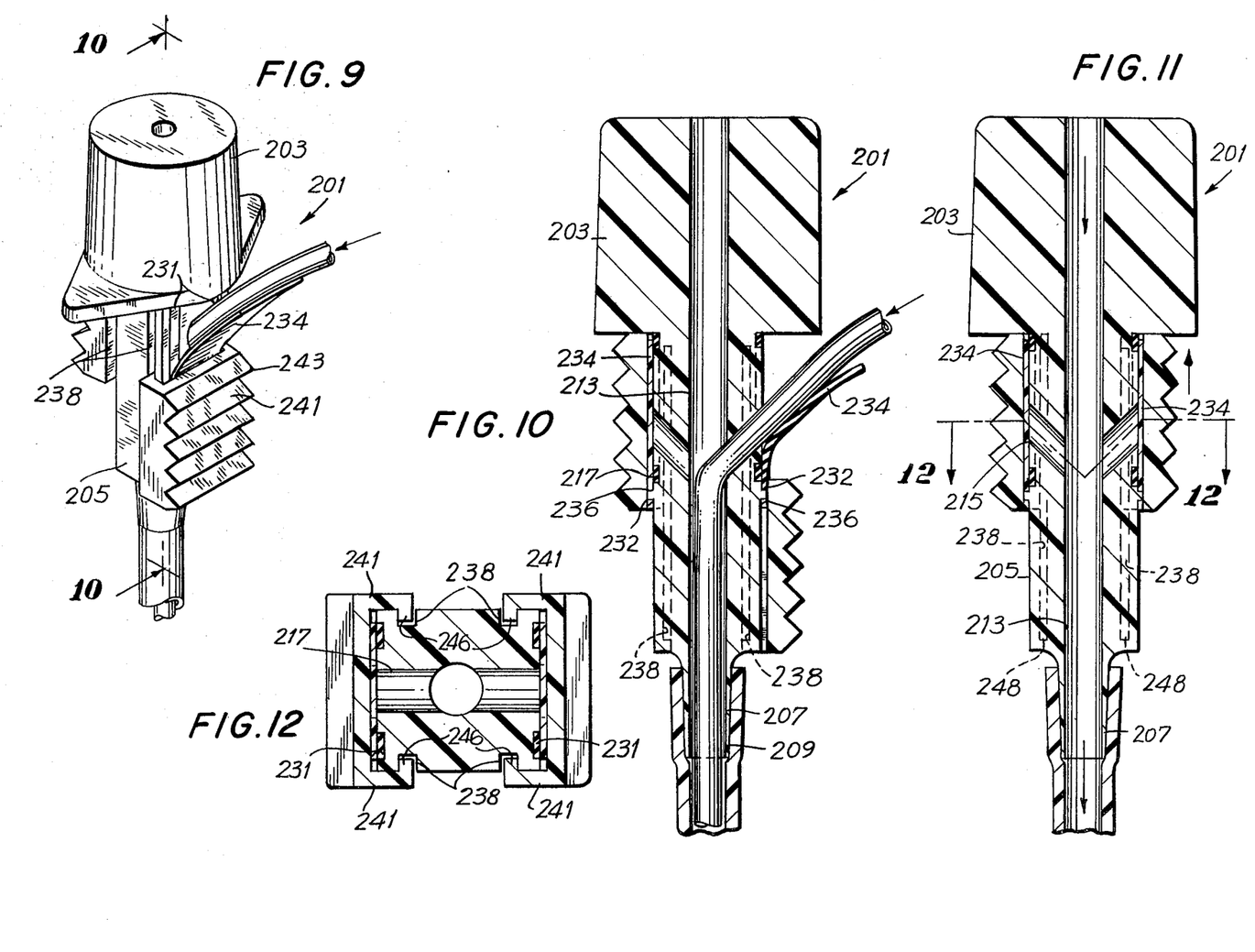
FIG. 9 is a perspective view of a third embodiment of the invention in one state of operation.
FIG. 10 is a sectioned elevation view of the third embodiment of the invention in the state shown in FIG. 9.
FIG. 11 is a sectioned elevation view of the third embodiment of the invention shown in another state of operation.
FIG. 12 is a sectioned plan view of the third embodiment of the invention taken through line 12—12 of FIG. 11.

In use the cylindrical collar 141 is normally maintained tightly over both of the O-rings 131 and rotated to a point where the pins 142 are disposed in respective ends of the groove sections 124 distant from the axial groove sections 122 as in FIGS. 9–11. The groove sections 124 may, at their distal ends, be provided with shoulder portions 144 to serve as catch points for the pins 142 thereby further preventing inadvertent rotation of the collar 141 with respect to the adapter body 101.

When it is desired to suction the patient to remove fluid accumulations, the collar 141 can be gripped by the user between thumb and forefinger and rotated so that the pins 142 travel the circumferential length of the groove sections 124 after which the collar 141 can be slid axially toward the artificial airway end of the adapter body 101 thereby exposing the adapter body access openings 115, as shown in FIG. 12. The cooperating tapers in the adapter body middle section 105 and the interior bore of the cylindrical collar 141 facilitate axial movement of the collar 141 relative to the adapter body 101 in a direction from the respirator end toward the artificial airway end of the adapter body. A catheter can then be positioned in either of the guideway grooves leading to the access openings 115 and inserted through the adapter and artificial airway as previously described in connection with the first preferred embodiment of the invention. When suctioning is completed the catheter can be withdrawn and the collar 141 raised as far as it will go and then twisted until firmly locked thereby forming an airtight seal permitting air and gas flow through the adapter without leakage. The suction adapter of the second embodiment can be operated with one hand which makes it particularly useful with neonates who are often kept in an environment conveniently accessible to only one hand of an attending nurse or physician.

A third embodiment of the invention will now be described with reference to FIGS. 9–12 in which there is shown adapter body 201 having a substantially rectangular cross-section with an enlarged portion 203 adapted to be removably connected to a respirator, a middle body portion 205 and a tapered body portion 207 terminating in a tapered fitting 209. The adapter body 201 has a cylindrical axial bore 213 and access openings 215 in each of two of its opposing sides which communicate with the axial bore 213 through inclined or sloping bores 217 which are angled as previously described in connection with the first and second embodiments of the invention. The sides of the middle portion 205 of the adapter body 201 include rectangular grooves framing each respective access opening 215 to accept a rectangular frame 231 made of an elastomeric material such as rubber. Extending outwardly from respective sides of the adapter body middle portion 205 are rectangular projections 232 which can be molded integrally with the adapter body 201.

Fitted on each of the rectangular projections 232 is a flat rectangular plastic tab 234 which has a rectangular aperture 236 dimensioned to fit snugly onto each rectangular projection 232. The tabs 234 are made of a resilient plastic and are normally bent in an arc tapering away from the adapter body middle section 205 in a direction from the artificial airway end to the respirator end as shown in FIGS. 9, 10 and 12.

Formed on each of the sides of the adapter body middle section 205 transverse to the sides having the access openings 215 are parallel spaced longitudinal grooves 238 extending from the enlarged body portion 203 to a region just short of the tapered portion 207.

A movable slide 241 has a serrated outer surface 243 adapted to be gripped by a user's thumb and inward extending legs 244 having tongue members 246 disposed in each pair of longitudinal grooves 238 on respective opposite sides of the adapter body middle section 205, the slides each spanning the adapter body middle portion surfaces in which the access openings 215 are disposed and on which the tabs 234 are mounted. Travel of each of the slides in a direction towards the artificial airway is limited by stops 248 in which the grooves 238 terminate and at the respirator end of the adapter body middle portion 205 by the enlarged adapter body portion 203.

As the slides 241 are moved axially from the artificial airway end of the adapter body 201 toward the respirator end, the resilient outward extending tabs 234 are urged inwardly by a cam action which occurs as the surface of the slide 241 facing the surface of the adapter body engages the tabs. As each tab is urged inwardly it engages a respective rectangular rubber frame 231 the surface of which protrudes slightly beyond the surface of the plastic adapter body middle section 205 and the rubber frame is compressed forming a substantially airtight seal between the adapter body middle portion 205 and the tab 234. The slide is held in place urging the tab 234 in sealing engagement with the rubber frame 231 by friction between the tab and slide enhanced by the resilient force of the tab exerted against the slide. The rectangular projection 232 can be dimensioned to extend sufficiently outward from the adapter body middle portion 205 to engage the slide 241 to prevent inadvertent slipping of the slide 241 absent application of intentional finger pressure.

As in the previously described first and second embodiments only one access opening and bore need be provided and hence only one tab and slide corresponding to the access opening are necessary. However, it has been found preferable to provide access openings on opposite sides of the adapter body so that the adapter need not be turned or turned a great degree to cause an access opening to face a suitable direction for catheter insertion.

In use of the third embodiment the slide 241 is normally maintained over the access opening 215 there urging the corresponding tab 234 against the rubber frame 231 to form an airtight seal whereby air and gases can flow between the respirator and patient without pressure loss or leakage through the adapter body 201 as shown in FIG. 11. When it is desired to suction the patient to remove accumulated body fluids the adapter body 201 can be grasped with one hand and a thumb placed on the serrated surface 243 of the slide 241 and the slide 241 can then be pushed toward the artificial airway thereby permitting the resilient tab 234 to separate from the rubber sealing frame 231 to expose the access opening 215 as shown in FIGS. 9 and 10. The catheter can then be inserted through the access opening as previously described in connection with the first and second embodiments and after suctioning is completed can be withdrawn. The slide 241 is then moved by thumb pressure along the track defined by grooves 238 to urge the tab 234 against the rubber frame and cover the access opening.

Figure 13:
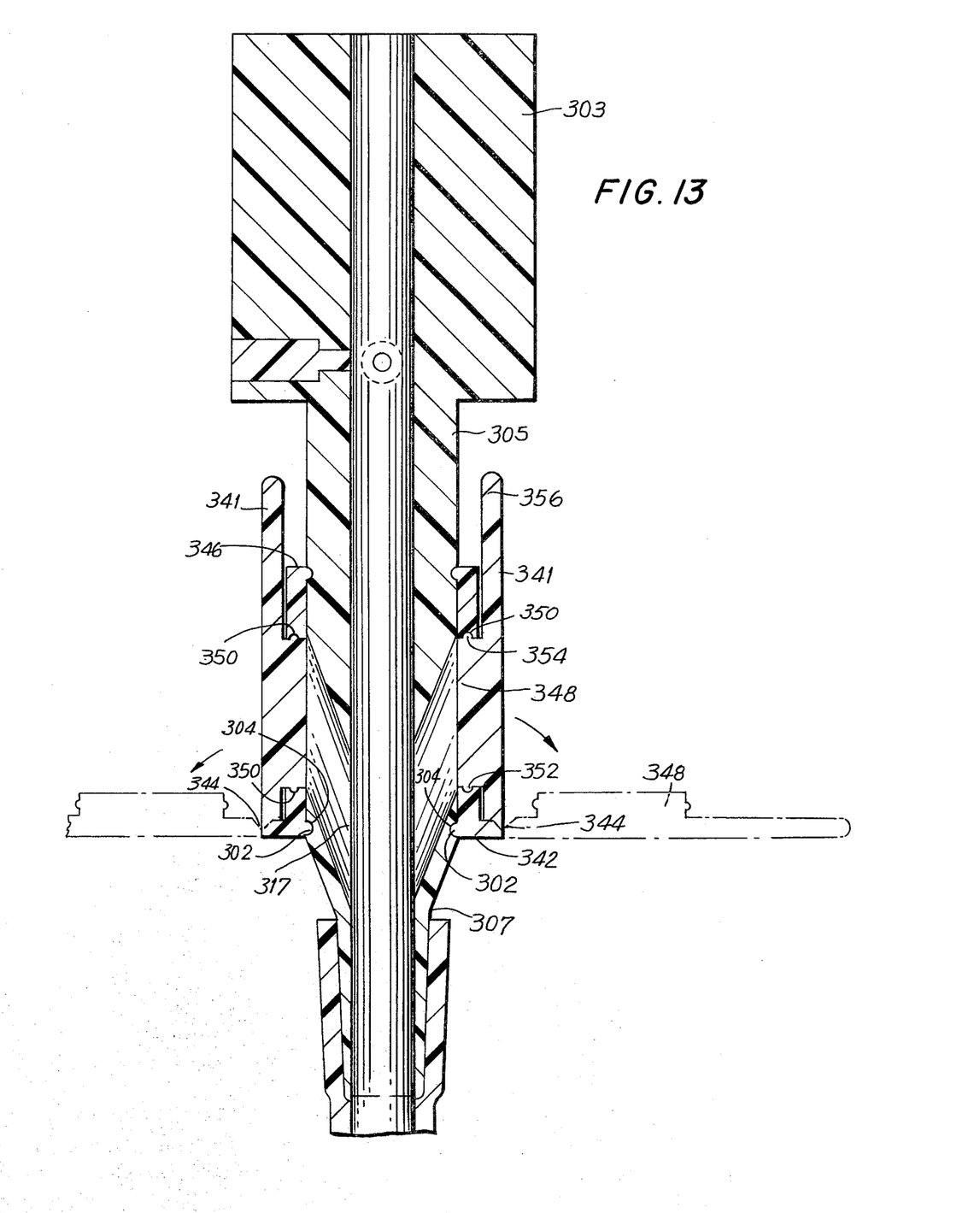
FIG. 13 is a sectioned elevation view of a fourth embodiment of the invention.

A fourth embodiment of the invention is shown in FIG. 13. The adapter of the fourth embodiment has a stepped cylindrical body with an upper portion 303 of enlarged diameter, a middle portion 305 and a lower tapered portion 307. Inclined bores 317 communicate with axial bore 313. The adapter body structure is similar to those of the previously described embodiments but a modified access closure means is employed to selectively seal and provide access to the inclined bores 317 for inserting a catheter in a manner previously described.

The access closure means includes respective members 341 each of which is pivotally mounted on a support member 342 which is in turn mounted on the circumference of the adapter middle portion 305. Each closure member 341 can be integrally moulded with the support member 342 which can be a ring circumscribing the adapter middle portion 305 and held in place by a lip 302 fitted into a circumferential groove on the cylindrical adapter body. Notches 344 can be formed on the closure members 341 to define pivot axes substantially transverse to the axis of said body and about which the respective closure members can be independently rotated between a closed position (shown in solid lines in FIG. 13) and an open position (shown in phantom). The closure members 341 can also be molded directly on the adapter body or they can each be separately fabricated and assembled to the adapter body.

A retaining member 346 which can be a ring axially displaced from the support member 342 is also provided on the circumference of the adapter middle portion 305. The members 342 and 346 are disposed on either side of the access openings leading to the bores 317.

Integral raised portions 348 are formed on the inner surfaces of the closure members 341 and are adapted to seal the access openings leading to bores 317 when the members 341 are in the closed position. Lips 350 formed on the raised portions 348 mate with a groove 352 on the support member 342 and a groove 354 on the retaining member 346 to hold the members 341 in the closed position. Either of the members 341 can be moved to its open position by grasping its end portion 356 and urging it outward and downward.

It is to be appreciated that alterations to and variations of the four embodiments described herein can be made without departing from the spirit and scope of the invention which is to be limited only by the following claims.

What is claimed is:

1. An adapter for removably connecting a tube to a respirator comprising:

a substantially straight elongated body having first and second open ends, means on said first end adapted to be connected to said respirator, means on aid second end adapted to be connected to said tube, said body having a sole, substantially straight hollow, unobstructed axial bore extending between said ends, an access opening, and an inclined bore communicating between said access opening and said axial bore whereby a catheter can be inserted through said access opening into said axial bore, and access closure means comprising a member adapted to be gripped by one or more fingers of a user, movably mounted on the periphery of said body for limited movement between a position covering said access opening and a position proximately adjacent to yet exposing said access opening, said body further including means disposed between said ends for positively preventing inadvertent movement of said closure means further away from said covering position than said proximately adjacent position when said access closure means is moved to said exposing position.

2. Apparatus according to claim 1 wherein the angle between the axes of said axial bore and said inclined bore is between 20 degrees and 35 degrees.

3. Apparatus according to claim 1 further comprising means for releaseably securing said movable member in said covering position.

4. Apparatus according to claim 3 further comprising elastomeric resilient sealing means compressably disposed between said body and said movable member at least when said movable member is in said covering position, said sealing means forming a substantially airtight seal between said access closure means and said body about said access opening.

5. Apparatus according to claim 4 wherein portions of said sealing means are disposed on opposite sides of said aperture whereby said tube can be received in said aperture between said portions.

6. Apparatus according to claim 5 wherein said securing means comprises said sealing means.

7. Apparatus according to either of claims 5 or 6 wherein one of the outer surface of said body and the inner surface of said movable member has a groove and the other of the outer surface of said body and the inner surface of said movable member has a projection in said groove to permit limited movement of said movable member between said covering and exposing positions.

8. Apparatus according to any of claims 1, 2, 3, 4, or 6 wherein said movable member comprises a cylindrical collar mounted for rotation about said body, said collar having an aperture in its wall located so that said collar aperture is in registration with said access opening when in said exposing position and said aperture is out of registration with said access opening when said movable member is in said covering position.

9. Apparatus according to either of claims 4 or 6 wherein said sealing means comprises a hollow cylindrical deformable sleeve disposed between and coaxial with said collar and said body and having an aperture in registration with said access opening.

10. Apparatus according to claim 9 further comprising cooperating means on said sleeve and on said body to substantially prevent relative rotation between said sleeve and said body about their common axis.

11. Apparatus according to claim 10 wherein said cooperating means comprises alternating axial ribs and grooves, the ribs of one of said sleeve and said body being disposed within the grooves of the other of said sleeve and said body.

12. Apparatus according to claims 4, or 6, wherein said movable member comprises a cylindrical collar coaxial with and slidably mounted on said body.

13. Apparatus according to claim 12 wherein one of the inner surface of said collar and the outer surface of said body has an axial groove formed thereon and the other of the inner surface of said collar and the outer surface of said body has a projection slidably disposed in said groove to restrict movement of said collar relative to said body to a predetermined path.

14. Apparatus according to claim 13 wherein said axial groove terminates at one end in a circumferential groove which permits rotation of said collar relative to said body for circumferentially displacing said projection with respect to said axial groove to prevent inadvertent sliding of said collar relative to said body.

15. Apparatus according to any od claims 1, 2 or 3 wherein said movable member is pivotally mounted with respect to said body for rotation about an axis substantially transverse to the axis of said body.

16. An adapter for removably connecting a tube to an external device comprising:
a body having one end adapted to be connected to said device, another end adapted to be connected to said tube, an axial bore extending between said ends, an access opening, and an inclined bore communicating between said access opening and said axial bore, and access closure means comprising a member adapted to be gripped by one or more fingers of a user, movably mounted on the periphery of said body for movement between a position covering said access opening and a position exposing said access opening, resilient sealing means compressably disposed between said body and said movable member at least when said movable member is in said covering position, said sealing means forming a substantially airtight seal between said access closure means and said body about said access opening, one of the outer surface of said body and the inner surface of said movable member having a groove and the other of the outer surface of said body and the inner surface of movable member having a projection in said groove to permit movement of said movable member between said covering and exposing positions, and a pressure member mounted on said body and at least partially disposed between said sealing means and said movable member when said movable member is in said covering position, said pressure member having a cam surface normally being resiliently urged transversely away from said sealing means and into the path of movement of said movable member and movable into engagement with said sealing means in response to movement of said movable member over said cam surface.

17. Apparatus according to claim 16 wherein said pressure member comprises a tab connected at one end to said body and tapering away from said body in the direction of movement of said movable member from said exposing position to said covering position, a length of said tab being urged against said sealing means as said movable member is moved from said exposing position to said covering position.

18. An adapter for removably connecting a tube to an external device comprising
a body having one end adapted to be connected to said device, another end adapted to be connected to said tube, an axial bore extending between said ends, an access opening, and an inclined bore communicating between said access opening and said axial bore, access closure means comprising a member adapted to be gripped by one or more fingers of a user, movably mounted on the periphery of said body for movement between a position covering said access opening and a position exposing said access opening, and a pressure member mounted on said body and at least partially disposed between said body and said movable member when said movable member is in said covering position, said pressure member having a cam surface normally being resiliently urged transversely away from said body and into the path of movement of said movable member for sealing said access opening only when said movable member is moved to said covering position.

* * * * *